United States Patent [19]

Frey

[11] 4,290,772

[45] Sep. 22, 1981

[54] REDUCING LIGHT SCATTER IN PHOTOMETRIC MEASUREMENTS INVOLVING SUSPENDED PARTICLES

[75] Inventor: Raymond Frey, Zurich, Switzerland

[73] Assignee: Contraves AG, Zürich, Switzerland

[21] Appl. No.: 80,188

[22] Filed: Oct. 1, 1979

[30] Foreign Application Priority Data

Nov. 1, 1978 [CH] Switzerland ............... 11239/78

[51] Int. Cl.³ ............... G01N 33/72; G01N 21/15; G01N 21/47
[52] U.S. Cl. ............... 23/230 B; 23/913; 252/408; 356/40; 424/11
[58] Field of Search ............... 23/230 B, 913; 424/11; 356/39, 40; 252/408

[56] References Cited

U.S. PATENT DOCUMENTS

| | | | |
|---|---|---|---|
| 4,099,917 | 7/1978 | Kim | 23/230 B |
| 4,184,848 | 1/1980 | Batz | 23/230 B |
| 4,185,964 | 1/1980 | Lancaster | 424/11 |

*Primary Examiner*—Sidney Marantz
*Attorney, Agent, or Firm*—Werner W. Kleeman

[57] ABSTRACT

A method of reducing scattered light during photometric measurements, especially during the photometric measurement of haemoglobin and a reagent for the performance of the method. To a suspension which is ready for a measurement operation there is admixed an additive which reduces the difference between the refractive index of the suspension and the mean refractive index of the suspended phase. The reagent for the photometric determination of the haemoglobin comprises a lysing agent, means for modifying the refractive index, means for stabilizing the leukocytes and a solvent. The reagent is admixed as an additive to a suspension of blood particles in an isotonic solvent.

5 Claims, No Drawings

REDUCING LIGHT SCATTER IN PHOTOMETRIC MEASUREMENTS INVOLVING SUSPENDED PARTICLES

BACKGROUND OF THE INVENTION

The present invention relates to a new and improved method of reducing scattered light during photometric measurement, especially photometric measurement of haemoglobin, and furthermore, pertains to a new and improved reagent useful for the performance of the aforementioned method.

The invention is in the field of photometry and relates to a method for reducing the scattering of light during photometric measurement, especially during the simultaneous determination of the haemoglobin concentration according to a photometric method and the leukocyte count by an electronic counting operation in a cell suspension which has been prepared by haemolysis and stabilized by a stabilizer.

The counting of red and white blood cells, frequently combined with the determination of the haemoglobin concentration, has been performed for a number of years with partially and fully automated systems. The whole blood which has been rendered noncoagulatable by an anti-coagulant agent, consists of cellular constituents, such as erythrocytes, leukocytes, thrombocytes and plasma containing dissolved constituents therein. For the counting and possible simultaneous size determination of the cellular constituents such must be advantageously prepared for such type analysis. Thus, for instance, the leukocytes and erythrocytes are present in a typical quantitative ratio between one and one thousand. Hence, counting of the leukocytes is appreciably disturbed or even rendered impossible due to the existence of the erythrocytes which prevail in a predominant number. Techniques are utilized which bring about an extensive elimination of the erythrocytes, without changing the quantity of leukocytes. One heretofore known procedure is haemolysation which destroys the form of the erythrocytes, that is to say, splits them into small pieces, without altering the leukocyte count. During the counting, for instance, according to electrical resistance methods, it is possible to detect the erythrocyte fragments as artifacts and to distinguish them from the count of the leukocytes. The haemoglobin which is released during the destruction of the erythrocytes can be ancillarily determined photometrically, through the addition of further reagents.

The simultaneous determination of the leukocytes and the haemoglobin concentration of samples which have been prepared in this manner is limited in time, normally such samples remain stable for about 20 minutes, and therefore, within this period of time it is necessary to perform the analysis.

A typical characteristic of the haemolytic methods is that unspecific turbidity arises owing to the large quantity of the fragments of the erythrocytes which are present in the solution, but also because of the leukocytes which remain intact and which are to be counted, and such has a disturbing effect during the photometric measurement of the haemoglobin. It is known from nephelometry that the light intensity, transmitted by the scattering solution, is proportional to the number of colloid particles and to the square of their volume (RAYLEIGH). The cell dissolution into fragments of different size and number, caused by haemolysis, thus produces an uncontrollable transmission loss of the irradiated suspension. The proportion of light in the blue spectral region, which proportion has been reduced by the dispersion, is not a major factor during haemoglobin measurement. If the formed cell fragments and also the morphologically altered leukocytes further change their volume following haemolysis, then this transmission loss additionally is dependent upon time. The measured extinction thus is associated with a nonsystematic and time-dependent error in the form of an additional pseudo extinction and cannot be satisfactorily compensated by callibration operations. This fault can amount to as much as 3% to 7% of the haemoglobin value.

SUMMARY OF THE INVENTION

Therefore, it is a primary object of the present invention to provide a new and improved method of reducing scattered light during photometric measurement, especially photometric measurement of haemoglobin.

A further object of the invention is to provide a new and improved reagent for the performance of the method.

Now in order to implement these and still further objects of the invention, which will become more readily apparent as the description proceeds, the inventive method for the reduction of the disturbance of a photometric measurement by the scattered light in a suspension which is to be measured having a respective refractive index related to a respective phase, is manifested by the features that there is admixed an additive having a refractive index outside of the range which is encompassed by the refractive index of the suspension agent and the mean refractive index of the suspended phases and in a quantity which reduces such range.

The reagent for the reduction of the disturbance of a photometric measurement by the effects of light scattering in a suspension of blood particles or cells in an isotonic suspension agent, contains a lysing agent, means for modifying the refractive index, means for stabilizing the leukocytes, and a solvent.

DETAILED DESCRIPTION OF THE PREFERRED EMBODIMENTS

Describing now the invention, for the simultaneous determination of the haemoglobin concentration and the leukocyte count there are performed the following procedures:

1. Erythrocytes are dissolved in cell fragments as small as possible, while simultaneously accomplishing morphological fixation of the leukocytes; and
2. The refractive index of the suspension agent or solution is accommodated to the refractive index of the erythrocyte fragments and to the refractive index of the stabilized leukocytes.

To perform the invention there is employed a reagent having for instance the following composition:

5 to 10 grams trimethyl tetradecyl ammonium bromide (lysing agent)
20 to 35 grams octylphenol decaethylene glycol ether (haemolysing emulgator)
240 to 350 ml formaldehyde 37% by weight in water (leukocyte stabilizer)
ad 1000 ml isotonic common salt solution (sodium chloride solution).

The lysing agent, as a quaternary ammonium compound, has a specific cell dissolving effect upon the erythrocytes, whereas the leukocytes, while morphologically altered, however remain in number.

The emulsifier modifies the refractive index of the suspension in such a manner that for a predetermined concentration the emulgator/suspension agent-solution has a similar refractive index as the cell material and there is reduced, below a tolerable fault boundary, the scattering of the light in the cell suspension. This modified refractive index can also be established with a different substance possessing a sufficiently large refractive index and the requisite solubility. An emulgator which has a specific haemolysing effect upon erythrocytes augments the haemolitic effect of the lysing agent. In this way there can be obtained a practically quantitative and rapid haemolysis.

The stabilizer has a conserving effect upon the leukocytes, owing to its aldehyde group, that is to say, the cells are morphologically fixed. The number of leukocytes present in the suspension is thus stabilized and can be determined with electronic means.

In order to contain an optimum effect, in other words a rapid and selective haemolysis of the erythrocytes, an extensive elimination of the turbidity and an adequate stability of the leukocyte count, the three reagent components must be present in the suspension in a balanced combination. This effect can be obtained within the concentration ranges given in the prior Example. If the reagent which has been fabricated in this way is added in a ratio of one part reagent to ninety nine parts of a blood sample prepared for measurement, then there occurs a rapid haemolysis, the haemoglobin is freed in its derivative present in the erythrocytes and the concentration determination can be directly carried out thereafter with the suitable method. The haemolysised and stabilized cell suspension for the determination of haemoglobin and leukocytes remains stable for about 30 to 60 minutes.

While there are shown and described present preferred embodiments of the invention, it is to be distinctly understood that the invention is not limited thereto, but may be otherwise variously embodied and practiced within the scope of the following claims. Accordingly,

What I claim is:

1. A method of reducing disturbances of photometric measurement due to scattered light in a suspension consisting of a suspension agent and a suspended phase comprising suspended particles, which suspension is to be photometrically measured, said suspension agent and said suspended phase each having a respective refractive index, comprising:
    adding a chemical component to the suspension, said chemical component having a refractive index outside of the range encompassed by the refractive index of the suspension agent and the mean refractive index of the suspended phase and in a quantity effective to reduce such range.

2. The method as defined in claim 1, wherein:
    the suspension is a suspension of haemolysed erythrocytes and stabilised leukocytes in an isotonic common salt solution; and
    the chemical component is a haemolysing emulsifier.

3. A reagent for reducing the disturbance due to scattered light of a photometric measurement of a suspension of blood particles in an isotonic suspension agent, said reagent containing:
    a lysing agent;
    a first chemical component for modifying the refractive index of the suspension;
    a second chemical component for stabilizing the leukocytes; and
    a solvent capable of dissolving said lysing agent and said first and second chemical components.

4. The reagent as defined in claim 3, wherein said chemical component for modifying the refractive index of said suspension is an haemolysing emulsifier.

5. The reagent as defined in claim 4, containing:
    5 to 10 grams trimethyl tetradecyl ammonium bromide as the lysing agent;
    20 to 35 grams octylphenol decaethylene glycol ether as the haemolysing emulsifier;
    240 to 350 ml formaldehyde solution comprising 37% by weight formaldehyde in water; and
    sufficient isotonic sodium chloride solution to make up 1000 ml of reagent.

* * * * *